US00RE39114E

(19) United States
(12) Reissued Patent
Barry et al.

(10) Patent Number: US RE39,114 E
(45) Date of Reissued Patent: *May 30, 2006

(54) EXPRESSION OF SUCROSE PHOSPHORYLASE IN PLANTS

(75) Inventors: Gerard Francis Barry, Alexandria, VA (US); Jan Willem de Weerd, Meridian, ID (US); Ganesh Murthy Kishore, St. Louis, MO (US); Marcia Lee Weldon, Ballwin, MO (US)

(73) Assignee: Monsanto Technology LLC, St. Louis, MO (US)

( * ) Notice: This patent is subject to a terminal disclaimer.

(21) Appl. No.: 10/443,787

(22) Filed: May 22, 2003

Related U.S. Patent Documents

Reissue of:
(64) Patent No.: 6,235,971
Issued: May 22, 2001
Appl. No.: 08/907,740
Filed: Aug. 8, 1997

U.S. Applications:
(63) Continuation-in-part of application No. 08/596,024, filed on Feb. 6, 1996, now Pat. No. 5,716,837, which is a continuation-in-part of application No. 08/386,860, filed on Feb. 10, 1995, now abandoned.

(51) Int. Cl.

| | |
|---|---|
| ***C12N 15/00*** | (2006.01) |
| ***C12N 15/29*** | (2006.01) |
| ***C12N 15/82*** | (2006.01) |
| ***C12N 15/31*** | (2006.01) |
| ***A01H 4/00*** | (2006.01) |

(52) U.S. Cl. ..... 800/278; 800/295; 800/298; 800/281; 800/284; 800/287; 800/288; 800/306; 800/312; 800/317.2; 800/317.4; 800/320.1; 800/320.3; 435/419; 435/488; 435/320.1; 435/69.1; 435/411; 435/412; 435/415; 435/417; 435/194; 536/23.2; 536/23.7; 536/24.1

(58) Field of Classification Search ..... 800/278, 800/295, 298, 281, 284, 306, 288, 320.1, 800/312, 317.2, 287, 317.4, 320.3; 435/419, 435/488, 320.1, 411, 69.1, 412, 415, 417, 435/194; 536/23.2, 23.7, 24.1
See application file for complete search history.

(56) References Cited

U.S. PATENT DOCUMENTS

| | | | | |
|---|---|---|---|---|
| 4,888,170 | A | 12/1989 | Curtiss, III | 424/93 |
| 5,349,123 | A | 9/1994 | Shewmaker et al. | 800/205 |
| 5,716,837 | A | 2/1998 | Barry et al. | 435/419 |
| 6,235,971 | B1 | 5/2001 | Barry et al. | 800/278 |

FOREIGN PATENT DOCUMENTS

| | | |
|---|---|---|
| EP | 0 442 592 | 8/1991 |
| EP | 0 634 491 | 1/1995 |
| WO | WO 90/02484 | 3/1990 |
| WO | WO 90/12084 | 10/1990 |
| WO | WO 91/19806 | 12/1991 |
| WO | WO 92/14831 | 9/1992 |
| WO | WO 93/06711 | 4/1993 |
| WO | WO 95/02696 | 1/1995 |

OTHER PUBLICATIONS

Ferretti, et al., "Sequence analysis of the Glucosyltransferase A Gene from *Streptococcus mutans* Ingbritt", *Infection and Immunity*, 56:1585–1588 (1988).
James et al., "Nucleotide sequence of the gtfA Gene from *S. mutans*GS–5", *Nucleic Acids Research*, 16:10398 (1988).
Russell et al., "*Streptococcus mutans* gtfA Gene Specifics Sucrose Phosphorylase", *Infection and Immunity*, 56:2763–2765 (1988).
Kitao, et al. *J. Fermentation and Bioengineering*, 73:179–184 (1992).
Kitano et al. "The syntheses of catechin–glucosides by transglycosylation with *Leuconostoc mesenteroides* sucrose phosphorylase". *Biosci. Biotechnol. Biochem.* 57:2010–2015 (1993).

*Primary Examiner*—David T. Fox
(74) *Attorney, Agent, or Firm*—Thomas E. Kelly; Howrey LLP

(57) ABSTRACT

Introducing sucrose phosphorylase activity into plants by transformation with a gene for the enzyme increases the rate of sucrose hydrolysis, leading to increased starch, oil, and/protein levels. Sucrose phosphorylase genes from Streptococcus mutans and Leuconostoc mesenteroides have been found particularly advantageous for use in the present invention. Surprisingly, in potatoes transformed to express these genes in tubers, reduced bruise discoloration susceptibility and increased uniformity of starch deposition throughout the tuber are achieved.

44 Claims, 1 Drawing Sheet

EXPRESSION OF SUCROSE PHOSPHORYLASE IN PLANTS

Matter enclosed in heavy brackets [ ] appears in the original patent but forms no part of this reissue specification; matter printed in italics indicates the additions made by reissue.

This application is a continuation-in-part of U.S. application Ser. No. 08/596,024 filed Feb. 6, 1996, now U.S. Pat. No. 5,716,837, which is a continuation-in-part of U.S. application Ser. No. 08/386,860 filed Feb. 10, 1995 now abandoned.

Recent advances in genetic engineering have provided the requisite tools to transform plants to contain foreign genes. It is now possible to produce plants which have unique characteristics of agronomic and crop processing importance. Certainly, one such advantageous trait is enhanced starch and/or solids content and quality in various crop plants. Another is enhanced oil and protein content of seeds of various crop plants.

Sucrose is the carbon storage unit which is transported from the source tissues of most plants to the sink tissues. In sink tissues it is hydrolyzed and the components used to build other, more complex storage units, primarily starch, protein, and oil. The hydrolysis is primarily accomplished by sucrose synthase which produces UDPglucose and fructose. UDPglucose is converted to glucose 1-phosphate by UDPglucose pyrophosphorylase.

The starch content of the sink tissues of various crop plants has been increased through the use of a gene encoding a bacterial ADPglucose pyrophosphorylase. See PCT Application WO 91/19806 (equivalent to U.S. Ser. No. 08/120,703, Kishore, incorporated herein by reference). This enzyme catalyzes the production of ADPglucose from glucose 1-phosphate. It has also been found that its expression during certain phases of seed development can decrease the oil content which is thought to be due to the shunting of raw material to the starch pathway with a concomitant decrease in its availability for oil production.

Bruising of potatoes is a phenomenon found during large-scale production, handling, and storage. The bruise is seen as a dark spot primarily in the cortex area of the tuber. Bruising can lead to loss of quality in the tuber, lower consumer acceptance of potatoes and potato products, and processing loss of tubers having excessive levels of bruising. It has been found that potato varieties with higher starch content have greater susceptibility to bruising. It would be desirable to decrease the level or incidence of bruising and particularly desirable to do so while increasing the starch content of the tuber.

A more uniform distribution of starch and solids within the potato tuber is also desirable. The pith or core of the potato generally has lower solids content that the outer or cortex region. When longitudinal strips are cut from the potato tuber to make french fries, the middle portions of these strips therefore have lower solids levels than the ends and this is especially true of strips cut from the center of the tuber. Strips with lower solids content or with regions of lower solids content require longer cooking times to achieve the same degree of acceptability to the consumer. These longer cooking times may result in over-cooking of the higher solids strips. Longer frying times also result in greater absorption of fat and therefore low solids strips and those with lower solids content regions will have a higher fat content. Higher fat content fries are a less nutritious food. In the manufacture of potato chips, slices are cut across the potato tuber and the non-uniform distribution of solids can result in a fried product with overcooked edges, undercooked centers, and a higher fat content (especially in the center). The non-uniform distribution of solids in the potato tuber also results in disproportionate losses of potato solids (from the cortex) during the peeling process.

Higher solids content is also desirable in tomato. Higher solids in the form of soluble (usually sugars and acids) and insoluble solids contribute to processing efficiency and the yield of products such as ketchup, paste, sauces, and salsa. These solids also contribute to the taste and texture of the processed products. Higher solids also contribute to the improved taste of fresh tomatoes.

Sucrose phosphorylase is a microbial enzyme which catalyzes production of glucose-1-phosphate directly from sucrose. Its activity has been observed in a wide range of bacterial and fungal species, and the enzyme has been isolated from a number of them (Pimentel et al., 1992; Vandamme et al., 1987). Genes for this enzyme, have been isolated from Agrobacterium spp. (Fournier et al., 1994, and references cited therein), Streptococcus mutans, denominated gtfA, (Russell et al., Perry et al.) and Leuconostoc mesenteroides, denominated spl (Kitao et al., 1992). Heterologous expression of the gene from S. mutans in E. coli is disclosed in U.S. Pat. No. 4,888,170 (Curtiss, 1989), incorporated herein by reference. The utility of the transformed microorganism is use as a vaccine against S. mutans.

It is an object of this invention to provide an improved means for increasing starch content of various plants. It is a still further object to provide a means of decreasing the sucrose content of seeds in oilseed crops resulting in a decrease in the level of undesirable carbohydrates such as stachyose and raffinose, while increasing the carbon available for oil and protein production. It is a still further object to provide novel DNA constructs which are useful in providing said means. It is a still further object to provide potato tubers which exhibit increased starch content more uniformly throughout the tuber. It is a still further object of this invention to provide potato tubers with a reduced susceptibility to bruising. It is a still further object of this invention to provide improved cereal crops, such as maize, rice, wheat, and barley.

SUMMARY OF THE INVENTION

The present invention provides DNA constructs which encode a sucrose phosphorylase (SP) enzyme and which are useful in producing enhanced starch content in plants. In another aspect of the present invention, seeds having a decreased level of sucrose and other carbohydrates, which will result in increased oil and protein content as a result of SP expression are provided.

In accomplishing the foregoing, there is provided, in accordance with one aspect of the present invention, a method of modifying the carbohydrate content of target tissues of transgenic plants, comprising the steps of:

(a) inserting into the genome of a plant cell a recombinant, double-stranded DNA molecule comprising in sequence
  (i) a promoter which functions in the cells of a target plant tissue,
  (ii) a structural DNA sequence that causes the production of an RNA sequence which encodes a sucrose phosphorylase enzyme,
  (iii) a 3' non-translated DNA sequence which functions in plant cells to cause transcriptional termination and the addition of polyadenylated nucleotides to the 3'end of the RNA sequence;

(b) obtaining transformed plant cells; and (c) regenerating from the transformed plant cells genetically transformed plants.

In another aspect of the present invention there is provided a recombinant, double-stranded DNA molecule comprising in sequence (i) a promoter which functions in the cells of a target plant tissue, (ii) a structural DNA sequence that causes the production of an RNA sequence which encodes a sucrose phosphorylase enzyme, (iii) a 3' non-translated DNA sequence which functions in plant cells to cause transcriptional termination and the addition of polyadenylated nucleotides to the 3' end of the RNA sequence.

There have also been provided, in accordance with another aspect of the present invention, transformed plant cells that contain DNA comprised of the above-mentioned elements (i), (ii), and (iii). In accordance with yet another aspect of the present invention, differentiated potato, tomato, and cereal plants are provided that have increased starch content in the tubers, fruit and seeds, respectively, and differentiated oilseed crop plants are provided that have decreased sucrose and oligosaccharides containing sucrose, such as stachyose and raffinose, in the seeds.

There have also been provided methods of increasing the starch content in the starch production organs of plants, such as the tuber of potato and the seed of cereals, and decreasing the sucrose levels in oilseed crop plants, such as soybean and canola, leading to increased oil and protein content. In carrying out the method in potato, it has unexpectedly been found that there is a more uniform distribution of starch as compared between the pith and the cortex of the tuber. In another aspect of the invention, a method of providing potatoes having a reduced susceptibility to bruising is provided.

An additional advantage of sucrose phosphorylase activity in sink tissue, such as the tuber of potato, is related to providing an increased, novel sucrose hydrolyzing activity having a much lower Km for sucrose (1–25 mM) than that for plant sucrose hydrolyzing enzymes, sucrose synthases and invertases, which have a $K_m$ in the range of 50–300 mM. This advantage is important in the establishment of and strength of such sink tissues, resulting potentially in yield enhancement.

DETAILED DESCRIPTION OF THE INVENTION

Figure 1:
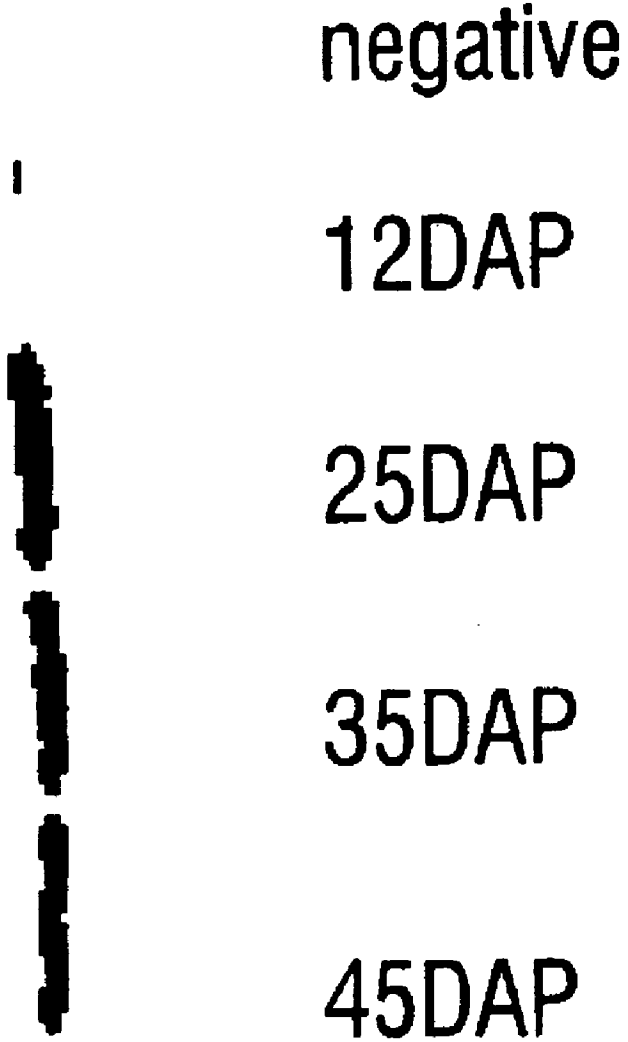
FIG. 1 refers to a western blot analysis of kernels sampled at 12, 25, 35 and 45 DAP.

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA.

Transcription of DNA into mRNA is regulated by a region of DNA usually referred to as the promoter. The promoter region contains a sequence of bases that signals RNA polymerase to associate with the DNA, and to initiate the transcription of mRNA using one of the DNA strands as a template to make a corresponding complimentary strand of RNA.

A number of promoters which are active in plant cells have been described in the literature. These include the nopaline synthase (NOS) and octopine synthase (OCS) promoters (which are carried on tumor-inducing plasmids of Agrobacterium tumefaciens), the caulimovirus promoters such as the cauliflower mosaic virus (CaMV) 19S and 35S and the figwort mosaic virus 35S-promoters, the light-inducible promoter from the small subunit of ribulose-1,5-bis-phosphate carboxylase (ssRUBISCO, a very abundant plant polypeptide), and the chlorophyll a/b binding protein gene promoter, etc. All of these promoters have been used to create various types of DNA constructs which have been expressed in plants; see, e.g., PCT publication WO 84/02913 (Rogers et al., Monsanto).

Promoters which are known or are found to cause transcription of DNA in plant cells can be used in the present invention. Such promoters may be obtained from a variety of sources such as plants and plant viruses and include, but are not limited to, the enhanced CaMV35S promoter and promoters isolated from plant genes such as ssRUBISCO genes. As described below, it is preferred that the particular promoter selected should be capable of causing sufficient expression to result in the production of an effective amount of sucrose phosphorylase (SP) enzyme to cause the desired increase in starch content. In addition, it is preferred to bring about expression of the SP gene in specific tissues of the plant such as root, tuber, seed, fruit, etc. and the promoter chosen should have the desired tissue and developmental specificity. Those skilled in the art will recognize that the amount of sucrose phosphorylase needed to induce the desired increase in starch content may vary with the type of plant and furthermore that too much sucrose phosphorylase activity may be deleterious to the plant. Therefore, promoter function should be optimized by selecting a promoter with the desired tissue expression capabilities and approximate promoter strength and selecting a transformant which produces the desired sucrose phosphorylase activity in the target tissues. This selection approach from the pool of transformants is routinely employed in expression of heterologous structural genes in plants since there is variation between transformants containing the same heterologous gene due to the site of gene insertion within the plant genome (commonly referred to as "position effect").

It is preferred that the promoters utilized in the double-stranded DNA molecules of the present invention have relatively high expression in tissues where the increased starch content and/or dry mater is desired, such as the tuber of the potato plant, the fruit of tomato, or seed of maize, wheat, rice, and barley. Expression of the double-stranded DNA molecules of the present invention by a constitutive promoter, expressing the DNA molecule in all or most of the tissues of the plant, will be rarely preferred and may, in some instances, be detrimental to plant growth.

The class I patatin promoter has been shown to be both highly active and tuber-specific (Bevan et al., 1986; Jefferson et al., 1990). A sequence of ~1.0 kb portion of the tuber-specific class I patatin promoter is preferred for tuber expression in the present invention. A number of other genes with tuber-specific or -enhanced expression are known, including the potato tuber ADPGPP genes, both the large and small subunits, (Muller et al., 1990), sucrose synthase (Salanoubat and Belliard, 1987, 1989), the major tuber proteins including the 22 kd protein complexes and proteinase inhibitors (Hannapel, 1990), the granule bound starch synthase gene (GBSS) (Rohde et al., 1990), and the other class I and II patatins (Rocha-Sosa et al., 1989; Mignery et al., 1988). Other promoters which are contemplated to be useful in this invention include those that show enhanced or specific expression in potato tubers, that are promoters normally associated with the expression of starch biosynthetic or modification enzyme genes, or that show different patterns of expression within the potato tuber. Examples of these promoters include those for the genes for the granule-bound and other starch synthases, the branching enzymes (Kossmann et al., 1991; Blennow, A. and Johansson, G., 1991; WO 92/14827; WO 92/11375), diproportionating enzyme (Takaha et al., 1993), debranching enzymes, amylases, starch phosphorylases (Nakano et al., 1989; Mori et al., 1991), pectin esterases (Ebbelaar, et al., 1993), the 40 kD glycoprotein, ubiquitin, aspartic proteinase inhibitor (Stukerlj et al., 1990), the carboxypeptidase inhibitors, tuber polyphenol oxidases (Shahar et al., 1992; GenBank® Accession Numbers M95196 and M95197), putative trypsin inhibitor and other tuber cDNAs (Stiekema et al., 1988), and for β-amylase and sporamins (from Ipomoea batatas; Yoshida et al., 1992; Ohta et al., 1991).

In addition, promoters may be identified to be tuber specific by screening a cDNA library of potato for genes which are selectively or preferably expressed in tubers and then determine the promoter regions to obtain tuber selective or tuber-enhanced promoters.

Other promoters can also be used to express a sucrose phosphorylase gene in specific tissues, such as seeds or fruits. β-conglycinin (also known as the 7S protein) is one of the major storage proteins in soybean (Glycine max) (Tierney, 1987). The promoter for β-conglycinin or other seed-specific promoters such as the napin and phaseolin promoters, can be used to over-express an SP gene specifically in seeds. This would lead to a decrease in the sucrose content of the seeds, which will result in a decrease in undesirable oligosaccharides and potentially an increase in the oil and/or protein content, which would be desirable in seeds used for oil or protein production such sa soybean, canola, oilseed rape, sunflower, safflower, etc. The SP gene will provide more raw material more quickly, but the plants own regulatory mechanisms will, unless influenced by other enzymes produced from heterologous genes, direct its use in the sink tissues.

The zeins are a group of storage proteins found in maize endosperm. Genomic clones for zein genes have been isolated (Pedersen, 1982), and the promoters from these clones, including the 15 kD, 16 kD, 19 kD, 22 kD, 27 kD, and gamma genes, could also be used to express an SP gene in the seeds of maize and other plants. Other promoters known to function in maize include the promoters for the following genes: waxy, Brittle, Shrunken 2, Branching enzymes I and II, starch synthases, debranching enzymes, oleosins, glutelins, and sucrose synthases. A particularly preferred promoter for maize endosperm expression of an SP gene is the promoter for a glutelin gene from rice, more particularly the Osgt-1 promoter (Zheng et al., 1993).

If one wanted to increase oil in maize seed, rather than starch, one would choose a promoter which causes expression of the SP gene during oil deposition. Such a promoter would be activated during the formation of the plant embryo. Examples of promoters active during embryogenesis are the promoters from the genes for globulin 1 and the late embryogenesis active (lea) proteins.

Examples of promoters suitable for expression of an SP gene in wheat include those for the genes for the ADPglucose pyrophosphorylase (ADPGPP) subunits, for the granule bound and other starch synthases, for the branching and debranching enzymes, for the embryogenesis-abundant proteins, for the gliadins, and for the glutenins. Examples of such promoters in rice include those for the genes for the ADPGPP subunits, for the granule bound and other starch synthases, for the branching enzymes, for the debranching enzymes, for sucrose synthases, and for the glutelins. A particularly preferred promoter is the promoter for rice glutelin, Osgt-1. Examples of such promoters for barley include those for the genes for the ADPGPP subunits, for the granule bound and other starch synthases, for the branching enzymes, for the debranching enzymes, for sucrose synthases, for the hordeins, for the embryo globulins, and the aleurone specific proteins.

The solids content of tomato fruit can be increased by expressing an SP gene behind a fruit specific promoter. The promoter from the 2A11 genomic clone (Pear, 1989) will control expression of ADPglucose pyrophosphorylase in tomato fruit. The E8 promoter (Deikman, 1988) would also express the SP gene in tomato fruits. In addition, promoters which function during the green fruit stage of tomatoes are disclosed in PCT Application PCTUS94/07072, filed Jun. 27, 1994, designating the U.S., incorporated herein by reference. They are designated TFM7 and TFM9. TFM7 which is a DNA fragment, isolated from tomato, of about 2.3 kb, of which 1.4 kb of the 3' end is shown in SEQ ID NO:3. TFM9 which is a DNA fragment of about 900 bp, of which 400 bp of the 3'end is shown in SEQ ID NO:4.

It is also now known that potato tuber promoters will function in tomato plants to cause fruit specific expression of an introduced gene. (See U.S. Ser. No. 08/344,639, Barry et al., filed Nov. 4, 1994, incorporated herein by reference.) Such promoters include potato patatin promoters, potato ADPGPP promoters, and potato granule bound starch synthase promoters. A particularly preferred promoter for tomato fruit expression is the promoter for the gene encoding the small subunit of ADPGPP in potato.

The solids content of root tissue can be increased by expressing an SP gene behind a root specific promoter. The promoter from the acid chitinase gene (Samac et al., 1990) would express the SP gene in root tissue. Expression in root tissue could also be accomplished by utilizing the root specific subdomains of the CaMV35S promoter that have been identified (Benfey et al., 1989).

The RNA produced by a DNA construct of the present invention may also contain a 5' non-translated leader sequence. This sequence can be derived from the promoter selected to express the gene, and can be specifically modified so as to increase translation of the nRNA. The 5' non-translated regions can also be obtained from viral RNAs, from suitable eukaryotic genes, or from a synthetic gene sequence. The present invention is not limited to constructs, as presented in the following examples, wherein the non-translated region is derived from the 5' non-translated sequence that accompanies the promoter sequence. Rather, the non-translated leader sequence can be derived from an unrelated promoter or coding sequence as discussed above.

Targeting Signal Sequences

An alternative method of increasing the rate of sucrose hydrolysis would be to target the SP to the apoplast. To do so requires a signal peptide is required on the N'-terminus of the functional protein. A preferred example of a sequence encoding such a signal sequence is a plant endoplasmic reticulum signal sequence from the PR-1B protein (Ohshima, et al., 1990). Thus the SP would be active in the apoplast and allow sucrose to be hydrolyzed extracellularly and allow for faster transport of glucose into the cell.

Another alternative is to target the SP to the vacuolar space. Targeting of the SP to the vacuole of a plant cell requires information in addition to the signal peptide (Nakamura and Matsuoka, 1993). A prepro-signal peptide could be fused to the amino terminus of the FT to target the enzyme to the vacuole (Sonnewald et al., 1991). Alternatively, a carboxy terminal sequence extension could be combined with an ER signal sequence to target the enzyme to the vacuole.

Sucrose Phosphorylases

As used herein, the term "sucrose phosphorylase" means an enzyme which catalyzes a reversible conversion of sucrose and inorganic phosphate to α-D-glucose-1-phosphate and D-fructose. It may be isolated from many microbial sources, including Streptococcus mutans, Clostridium pasteurianum (Vandamme et al., 1987), Pseudomonas saccharophila (Silverstein et al.), Pseudomonas putrifaciens, Pullularia pullulans, Acetobacter xylinum (Vandamme et al., 1987), Agrobacterium sp. (Fournier et al., 1994), and Leuconostoc mesenteroides.

The gene for the SP enzyme may be obtained by known methods and has already been isolated from several organisms, such as Agrobacterium sp. (Fournier et al., 1994) and Leuconostoc mesenteroides (Kitao et al., 1992). The gene from S. mutans has been expressed in E. coli (Robeson et al., 1983), identifying the activity as a glucosyl transferase. The isolation and use of SP coding sequences from Streptococcus mutans (gtfA) and Leuconostoc mesenteroides (spl) is described in the Examples below. These genes have been found to be particularly useful in accordance with the methods of the present invention. Their sequences are shown in SEQ ID NO:5 and SEQ ID NO:6, respectively. These and other SP genes can be used for insertion into plant expression vectors suitable for a transformation method of choice as described below.

A gene encoding SP (ORF 488) has been identified in the Ti plasmids of Agrobacterium vitus (formerly A. tumefaciens biotype 3). Related sequences have been reported in the Ti plasmids of other A. tumefaciens strains, in particular pTiC58 (Fournier et al., 1994). It is likely that a gene encoding SP may be found on all such plasmids.

Purification of the SP enzyme has been demonstrated from other bacterial and fungal sources (described above). The availability of such materials renders facile the subsequent cloning of the gene for this enzyme: the protein may be used as an immunogen to raise antibodies that may be used to identify clones in expression-based libraries such as λgt11 (Sambrook et al.); peptide sequences at the N-terminus of such proteins may be obtained by routine protein sequencing; and, following well established limited proteolysis procedures, the sequences of internal regions may also be determined. Such sequences may be used in the design of nucleotide probes or primers that may be used to identify the genes from clone banks or to amplify the gene or portions of the gene from RNA, cDNA, or DNA preparations from the source organism. Detection of E. coli containing sucrose phosphorylase clones is also possible by growth on minimal medium with sucrose as the sole carbon source (Ferretti, et al. 1988).

Other microorganisms that use SP to hydrolyze sucrose can be found by assaying for organisms which can utilize sucrose as the sole carbon source (Russell et al.). The protein can be isolated by following the enzymatic activity in the fractions using known methods. The gene encoding the protein can then be isolated as just described.

Thus, many different genes which encode an protein having sucrose phosphorylase activity may be isolated and used in the present invention.

Polyadenylation Signal

The 3' non-translated region of the chimeric plant gene contains a polyadenylation signal which functions in plants to cause the addition of polyadenylate nucleotides to the 3' end of the RNA. Examples of suitable 3' regions are (1) the 3' transcribed, non-translated regions containing the polyadenylated signal of Agrobacterium the tumor-inducing (Ti) plasmid genes, such as the nopaline synthase (NOS) gene, and (2) plant genes like the soybean storage protein genes and the small subunit of the ribulose-1,5-bisphosphate carboxylase (ssRUBISCO) gene. An example of a preferred 3' region is that from the ssRUBISCO gene of pea, also known as the E9 3' region.

Synthetic Gene Construction

The SP gene from Streptococcus mutans is high in A+T content, which may be inimical to high level expression in plant cells, although as shown below, the gene is expressed at levels sufficient to positively affect starch content. If desired, the gene sequence of the SP gene can be changed without changing the protein sequence in such a manner as may increase expression, and thus even more positively affect starch content in transformed plants. The rules for making the changes in the gene sequence are set out in WO 90/10076 (Fischhoff et al.). A gene synthesized by following the rules set out therein may be introduced into plants as described below and result in higher levels of expression of the SP enzyme. This may be particularly useful in monocots such as maize, rice, wheat, and barley.

Combinations with Other Transgenes

The effect of SP in transgenic plants can be enhanced by combining it with other genes which positively affect starch and/or oil content. For example, a gene which will increase ADPglucose pyrophosphorylase (ADPGPP) activity in plants may be used in combination with an SP gene to increase starch. Such ADPGPP genes include the E. coli glgC gene and its mutant glgC16. WO 91/19806 discloses how to incorporate this gene into many plant species in order to increase starch and/or solids.

Another gene which can be combined with SP to increase starch is a gene for sucrose phosphate synthase (SPS) which can be obtained from plants. WO 92/16631 discloses one such gene and its use in transgenic plants.

Another gene which can be combined with SP to increase oil is a gene for acetyl CoA carboxylase, which can be obtained from plants. WO 93/11243 discloses one such gene.

Plant Transformation/Regeneration Plant Transformation/Regeneration

Plants which can be made to have increased polysaccharide (e.g. starch) content by practice of the present invention include, but are not limited to, maize, wheat, rice, tomato, potato, sweet potato, peanut, barley, cotton, strawberry, raspberry, and cassava. Plants which can be made to have modified carbohydrate content by practice of the present invention include, but are not limited to, maize, wheat, rice, tomato, potato, sweet potato, peanut, barley, sugarbeet, sugarcane, apple, pear, orange, grape, cotton, strawberry, raspberry, and cassava. Plants which can be made to have reduced bruising discoloration by practice of the present invention include, but are not limited to, wheat, potato, sweet potato, barley, sugarbeet, sugarcane, apple, pear, peach, orange, grape, banana, plantain, and cassava. Plants which can be made to have improved uniform solids content by practice of the present invention include, but are not limited to potato, sweet potato, banana, plantain, and cassava. Plants which can be made to have increased yield of harvested material by practice of the present invention include, but are not limited to, maize, wheat, rice, tomato, potato, sweet potato, peanut, barley, sugarbeet, sugarcane, apple, pear, orange, peach, banana, plantain, grape, cotton, strawberry, raspberry, and cassava. Plants which can be made to have decreased sucrose leading to increased oil or protein content include soybean, maize, canola, and sunflower.

A double-stranded DNA molecule of the present invention containing an SP gene can be inserted into the genome of a plant by any suitable method. Suitable plant transformation vectors include those derived from a Ti plasmid of Agrobacterium tumefaciens, as well as those disclosed, e.g., by Herrera-Estrella (1983), Bevan (1984), Klee (1985) and EPO publication 120,516 (Schilperoort et al.). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen.

A plasmid expression vector, suitable for the introduction of an SP gene in monocots using microprojectile bombardment is composed of the following: a promoter that is specific or enhanced for expression in the starch storage tissues in monocots, generally the endosperm, such as promoters for the zein genes found in the maize endosperm (Pedersen et al., 1982); an intron that provides a splice site to facilitate expression of the gene, such as the Hsp70 intron (PCT Publication WO93/19189); and a 3' polyadenylation sequence such as the nopaline synthase 3' sequence (NOS 3'; Fraley et al., 1983). This expression cassette may be assembled on high copy replicons suitable for the production of large quantities of DNA.

A particularly useful Agrobacterium-based plant transformation vector for use in transformation of dicotyledonous plants is plasmid vector pMON530 (Rogers, S. G., 1987). Plasmid pMON530 is a derivative of pMON505 prepared by transferring the 2.3 kb StuI-HindIII fragment of pMON316 (Rogers, S. G., 1987) into pMON526. Plasmid pMON526 is a simple derivative of pMON505 in which the SmaI site is removed by digestion with XmaI, treatment with Klenow polymerase and ligation. Plasmid pMON530 retains all the properties of pMON505 and the CaMV35S-NOS expression cassette and now contains a unique cleavage site for SmaI between the promoter and polyadenylation signal.

Binary vector pMON505 is a derivative of pMON200 (Rogers, S.G., 1987) in which the Ti plasmid homology region, LIH, has been replaced with a 3.8 kb HindIII to SmaI segment of the mini RK2 plasmid, pTJS75 (Schmidhauser & Helinski, 1985). This segment contains the RK2 origin of replication, oriV, and the origin of transfer, oriT, for conjugation into Agrobacterium using the tri-parental mating procedure (Horsch & Klee, 1986). Plasmid pMON505 retains all the important features of pMON200 including the synthetic multi-linker for insertion of desired DNA fragments, the chimeric NOS/NPTII'/NOS gene for kanamycin resistance in plant cells, the spectinomycin/streptomycin resistance determinant for selection in E. coli and A. tumefaciens, an intact nopaline synthase gene for facile scoring of transformants and inheritance in progeny and a pBR322 origin of replication for ease in making large amounts of the vector in E. coli. Plasmid pMON505 contains a single T-DNA border derived from the right end of the pTiT37 nopaline-type T-DNA. Southern analyses have shown that plasmid pMON505 and any DNA that it carries are integrated into the plant genome, that is, the entire plasmid is the T-DNA that is inserted into the plant genome. One end of the integrated DNA is located between the right border sequence and the nopaline synthase gene and the other end is between the border sequence and the pBR322 sequences.

Another particularly useful Ti plasmid cassette vector is pMON17227. This vector is described by Barry et al. in WO 92/04449 (corresponding to U.S. Ser. No. 07/749,611, incorporated herein by reference) and contains a gene encoding an enzyme conferring glyphosate resistance (denominated CP4) which is an excellent selection marker gene for many plants, including potato and tomato. The gene is fused to the Arabidopsis EPSPS chloroplast transit peptide (CTP2) and expressed from the FMV promoter as described therein.

When adequate numbers of cells (or protoplasts) containing the SP gene or cDNA are obtained, the cells (or protoplasts) are regenerated into whole plants. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, canola/rapeseed, etc.), Cucurbitaceae (melons and cucumber), Gramineae (wheat, barley, rice, maize, etc.), Solanaceae (potato, tobacco, tomato, peppers), various floral crops, such as sunflower, and nut-bearing trees, such as almonds, cashews, walnuts, and pecans. See, e.g., Ammirato, 1984; Shimamoto, 1989; Fromm, 1990; Vasil, 1990; Vasil, 1992; Hayashimoto, 1989; Shimamoto, 1989; and Datta, 1990.

The following examples are provided to better elucidate the practice of the present invention and should not be interpreted in any way to limit the scope of the present invention. Those skilled in the art will recognize that various modifications, truncations, etc. can be made to the methods and genes described herein while not departing from the spirit and scope of the present invention.

All basic DNA manipulations and genetic techniques described in the Examples provided herein, unless otherwise stated, such as PCR, agarose electrophoresis, restriction digests, ligations, E. coli transformations, Western blots etc. were performed by standard protocols as described in Sambrook et al. (1989) and/or Maniatis et al. (1982).

EXAMPLES

Example 1

A sucrose phosphorylase gene, gtfA, was generated by PCR amplification from Streptococcus mutans cells. The gene was amplified using the 5' oligonucleotide:

5CCCGGATCCATGGCAATTACAAATAAAAC (SEQ ID NO:1) and the 3' oligonucleotide:

5'GGGGAGCTCACTCGAAGCTTAT-TGTTTGATCATTTTCTG (SEQ ID NO:2)

The PCR cycling conditions were as follows: 94° C., 3';55° C., 2';72° C., 2' (5 cycles);94° C. 1';55° C. 2';72° C. 2' (30 cycles). The 1462 bp PCR product was purified using the GeneClean purification system (Bio101, Vista, Calif.), digested with BamHI and SacI, and ligated into the BamHI and SacI sites of pUC119. The ligated DNA was transformed into JM101 and a blue-white screen was used to identify colonies for plasmid preparation and restriction digestion. Digestion with HindIII was used to screen for transformants containing the gtfA gene. Clones with correct restriction patterns were screened for phenotypic expression by the ability to utilize sucrose as sole carbon source as follows: clones were transformed into a gal-E. coli strain, SK1592, and grown on minimal medium containing raffinose (which is taken up and hydrolyzed to galactose and sucrose) and an active clone was identified and named pMON17353.

An expression cassette was constructed to allow for constitutive expression of gtfA in plants. A fragment containing the enhanced 35S promoter (Kay, R. 1987), the Nopaline synthase 3' region (Bevan, M. 1984), and the pUC vector backbone was prepared from pMON999 (Rogers et al., 1987a) by restriction digestion with BglII and SacI. A fragment containing the gtfA coding region was prepared from pMON17353 by restriction digestion with BamHI and SacI. The correct fragments were separated by agarose gel electrophoresis and purified by the GeneClean procedure. The fragments were ligated, transformed into E. coli JM 101, and putative recombinant plasmids were screened by restriction digestion with NotI. One clone was identified and named pMON17359.

A second expression cassette was constructed to direct expression of gtfA to the potato tuber. A fragment containing the patatin 1.0 promoter (described above), the Nopaline synthase 3' region, and the pUC vector backbone was prepared from an intermediate vector by restriction digestion with BamHI and SacI. An expression cassette was also constructed to direct expression of gtfA to the tomato fruit. A fragment containing the TFM7 promoter, the Nopaline synthase 3' region, and the pUC vector backbone was prepared from pMON16987 (PCT Application PCTUS94/07072, filed Jun. 27, 1994), which is derived from pMON999 but contains the TFM7 promoter, by restriction digestion with BglII and SacI. The correct fragments were separated by agarose gel electrophoresis and purified by the GeneClean procedure. These fragments were each ligated to the BamHI and SacI fragment from pMON17353. Transformation and screening of clones were as described above. Clones were designated as correct and named pMON17356 (Pat 1.0/gtfA/NOS) and pMON17389 (TFM7/gtfA/NOS).

A third expression cassette was constructed to direct expression of gtfA to the potato tuber using a 3.5 kb promoter of patatin. The patatin 3.5 promoter was obtained from the plasmid pBI240.7 (Bevan et al., 1986). The majority of the 3.5 promoter was excised from pBI240.7, from the HindIII site (at~3500) to the XbaI site at −337, and combined with the remainder of the promoter, from the XbaI site to a BglII site at +22 (formerly a DraI site), in a triple ligation into a vector which provided a BglII site to form pMON17280. An intermediate vector was prepared by digestion of pMON17353 with BamHI/SacI and insertion of the fragment into pBS. This vector was then digested with EcoRI and SacI. pMON17280 was digested with EcoRI and SacI resulted in a fragment containing the patatin 3.5 promoter, the Nopaline synthase 3' region, and the pUC vector backbone. The correct sized fragments were obtained by agarose gel electrophoresis and the GeneClean procedure. The fragments were ligated, transformed into E. coli JM101, and screened by restriction digestion with HindIII. One clone was designated as correct and named pMON17495.

In pMON17356, pMON17359, pMON17389, and pMON17495, the promoter, gtfA gene and the Nos 3' region can be isolated on a NotI restriction fragment. These fragments can then be inserted into a unique NotI site of either vector pMON17227 (described above) or pMON17320 to construct glyphosate selectable plant transformation vectors. pMON17320 is a pMON17227 derivative which also contains a Patatin 1.0/CTP1-glgC16 cassette. The CTP1-glgC16 fusion encodes a modified ADPglucose pyrophosphorylase as described by Kishore in WO 91/19806. A vector was also constructed for tomato expression of gtfA by combining the gtfA gene and 3' region from pMON17356 with the ~2.0 kp potato small ADPglucose pyrophosphorylase subunit gene promoter (See U.S. Ser. No. 08/344,639, Barry et al., filed Nov. 4, 1994, incorporated herein by reference.) in a plant transformation vector to form pMON17486.

The vector DNA is prepared by digestion with NotI followed by treatment with calf intestinal alkaline phosphatase (CIAP). The gtfA containing fragments are prepared by digestion with NotI, agarose gel electrophoresis and purification with GeneClean. Vector and insert DNA is ligated, transformed into the E. coli strain LE392, and transformants were screened by restriction digestion to identify clones containing the gtfA expression cassettes. Clones in which transcription from the gtfA cassette is in the same direction as transcription from the selectable marker were designated as correct and named pMON17357 (FMV/CP4/E9, Pat1.0/gtfA/NOS), pMON17358 (Pat1.0/CTP1-glgC16/E9, Pat1.0/gtfA/NOS, FMV/CP4/E9), pMON17360 (FMV/CP4/E9, E35S/gtfA/NOS), pMON17390 (FMV/CP4/E9, TFM7/gtfA/NOS), pMON17392 (Pat1.0/CTP1-glgC16/E9, TFM7/gtfA/NOS, FMV/CP4/E9), and pMON17496 (FMV/CP4/E9, Pat 3.5/gtfA/NOS).

A transformation vector was constructed to direct expression of gtfA in maize seed. A fragment containing the glutelin promoter Osgt-1, Hsp70 intron (described above). Nopaline synthase 3' region, kanamycin resistance, and pUC backbone was prepared by restriction digestion, agarose gel electrophoresis, and GeneClean. A fragment containing the gtfA coding region was prepared from pMON17359 by restriction digestion with NcoI and NotI. The fragments were ligated, transformed and screened by restriction digestion. A correct clone was identified and named pMON24502 (Osgt1/Hsp70/gtfA/NOS).

A transformation vector was constructed to direct expression of gtfA in seeds of oilseed crops. A BamHI-EcoRI fragment of pMON17353 was ligated into the BglII-EcoRI sites of an intermediate vector to give pMON26104 which placed the gtfA gene behind the 7s promoter (discussed above) and used the E9 3' terminator sequence. A NotI fragment containing the FMV promoter, the fusion of the CTP2 and glyphosate resistance gene and a Nos 3' sequence, was ligated into the NotI site of pMON26104 to give pMON26106, a double border plant transformation vector with both of the cassettes in the same orientation.

Example 2

The vector pMON17357 was transformed into Russet Burbank potato callus following the method described by Barry et al. in WO 94/28149 for glyphosate selection of transformed lines. A number of lines were obtained and evaluated in field tests. The results of this test are shown in Table 1. As can be seen therein, several lines were identified as containing higher starch levels (measured as total solids) and some of those had decreased bruising.

TABLE 1

| Line Identification | Solids (%) Mean | Bruising Index Mean |
|---|---|---|
| Control | 21.9 | 3.399 |
| 1 | 22.9 | 3.798 |
| 3 | 22.2 | 3.479 |
| 4 | 23.3 | 2.899 |
| 6 | 21.8 | 2.798 |
| 8 | 22.7 | 2.979 |
| 11 | 21.6 | 2.968 |
| 12 | 22.0 | 3.383 |
| 14 | 22.3 | 3.218 |

TABLE 1-continued

| Line Identification | Solids (%) Mean | Bruising Index Mean |
|---|---|---|
| 15 | 22.7 | 2.979 |
| 17 | 22.3 | 3.394 |
| 18 | 21.7 | 3.394 |
| 19 | 22.4 | 3.213 |
| 22 | 22.7 | 3.503 |

Tubers from twelve lines were tested for any change in the distribution of starch between the pith or cortex. This was accomplished by peeling the tubers, cutting them into strips resembling french fries, and measuring solids using a brine flotation comparison test. The average solids level for strips from the pith was subtracted from the average solids level for strips from the cortex. Thus a difference in solids which is less than that for the control (4.61% in this test) is an indication of more uniform distribution of starch in the tuber, which is highly desirable. The results are shown in Table 2. As can be seen, the difference in solids between the cortex and the pith was reduced in ten of the twelve lines.

TABLE 2

| Line | Solids Difference (%) |
|---|---|
| Control | 4.61 |
| 3 | 4.53 |
| 4 | 4.16 |
| 6 | 3.57 |
| 8 | 3.20 |
| 11 | 3.94 |
| 12 | 4.39 |
| 14 | 4.67 |
| 15 | 3.56 |
| 17 | 2.61 |
| 18 | 3.79 |
| 19 | 5.19 |
| 22 | 3.92 |

Five of these lines were tested the next year in the field, four of them in multiple locations. (Line number 8 was tested in only one location). The absolute increase in solids in those five lines, indicating an increase in starch content, was again demonstrated in each line. The results are shown in Table 3.

TABLE 3

| Line | Solids increase |
|---|---|
| 1 | 0.256 |
| 4 | 0.856 |
| 8 | 2.61 |
| 15 | 0.211 |
| 22 | 0.162 |

Example 3

Expression of gtfA in corn introduces a novel catalytic activity which may facilitate sucrose import into the endosperm by creating a steeper concentration gradient and conserve energy since the equivalent of one mole of ATP is normally required to convert sucrose to a hexose plus a hexose phosphate. The vector pMON24502 has been introduced into maize cells by microprojectile bombardment using two different types of embryogenic callus tissue for transformation. It was cotransformed with either (1) pMON19476 which contains a selection cassette of the enhanced 35S promoter, the Hsp 70 intron, the NPTII coding sequence for kanamycin resistance, and the nos 3' sequence or (2) pMON19336 which contains two selection cassettes for glyphosate resistance, each using the rice actin promoter and the Hsp70 intron, but one uses a gene encoding glyphosate oxidase and one uses the CP4 glyphosate resistance gene.

(1) Immature maize embryos (H99 genotype) were isolated as described in EP 586 355 A2. Embryogenic callus was obtained by culturing the immature embryos for about two weeks on the medium described by Duncan et al. (1985), called Medium D. After 2 weeks, callus (Type I) is obtained and is maintained by subculturing every 2–3 weeks onto fresh Medium D. Approximately four hours prior to bombardment, actively growing callus (mid subculture cycle) is placed on Medium D with added mannitol and sorbitol for osmotic pretreatment. Approximately 16–24 hours after bombardment with particles coated with pMON24502 and pMON19476, the tissue is placed on Medium D without mannitol or sorbitol. Approximately two days later, the tissue is transferred onto Medium D containing paromomycin. Resistant tissue is transferred to fresh Medium D with paromomycin at approximately three week intervals. Plant regeneration is accomplished on Medium D with 6-benzylaminopurine (without dicamba) for a 3–6 day "pulse", followed by placement on MS medium without hormones.

(2) Type II callus, derived from immature embryos of the "Hi-II" genotype, is used by following the method of Dennehy et al., 1994. Type II callus was pretreated on N6 1-100-25 medium containing 0.4 M mannitol+sorbitol (0.2 M of each) for four hours prior to bombardment with pMON24502 and pMON19336 and left on this same medium for 16 to 24 hours after bombardment. The tissue was then transferred to N6 1-100-25 medium without added mannitol or sorbitol. Selection was accomplished using 1–3 mM glyphosate in N6 1-0-25 medium (containing no casamino acids).

Fertile maize plants have been obtained by each method and their seeds tested. Production of the GtfA protein was confirmed by Western blot analysis using goat antibody raised against E. coli-expressed gtfA. Of the 16 lines screened, 9 express GftA, at approximately 0.05 to 0.5% of the total cellular protein. The starch biosynthetic rate in maize endosperm tissue expressing GftA (sucrose phosphorylase) was measured in vitro using a sugar feeding assay which has been described previously (Felker, et al., 1990). Field grown plants were screened by PCR to identify the positive and negative segregants. Positive and control ears from two GftA transformed lines (Knowl and De) were harvested at 20 to 22 days post pollination, at the time of linear grain fill. Endosperm sections were recovered and were fed $^{14}$C-sucrose at concentrations of 50 and 200 mM. The 200 mM concentration is the most physiologically relevant but due to the lower Km of GftA for sucrose than the endogenous enzymes, the lower concentration (50 mM) was used to improve the likelihood of measuring an effect from GftA. Time points were taken at one and two hours after feeding $^{14}$C and the radioactivity incorporated into the starch fraction was determined. The results with the two lines, are summarized in the following Table (data reported as average counts incorporated into starch fraction):

TABLE 4A

| Feeding with 50 mM sucrose | | |
|---|---|---|
| time of sampling | control | |
| | | Knowl |
| 1 hr | 9033 | 20895 |
| 2 hr | 15947 | 26695 |
| | | De |
| 1 hr | 10909 | 10860 |
| 2 hr | 19193 | 24284 |

TABLE 4B

| Feeding with 200 mM sucrose | | |
|---|---|---|
| time of sampling | control | |
| | | Knowl |
| 1 hr | 9880 | 12980 |
| 2 hr | 11175 | 21407 |
| | | De |
| 1 hr | 7703 | 7471 |
| 2 hr | 11038 | 13007 |

The results demonstrate that corn endosperm tissues expressing GtfA can produce starch at a more rapid rate (two-fold) than controls. The differences in starch rate are more apparent at the lower substrate concentrations, potentially due to the differences in substrate kinetics between GtfA and the endogenous sucrose synthase. Differences were also noted when comparing the effects in the lines De and Knowl, with Knowl displaying a more positive effect. GtfA protein was very high in Knowl, in the range of 0.5% of the total protein, whereas GtfA levels in De were in the range of 0.05%. The differences in starch biosynthetic rates are likely a function of GtfA expression levels.

Example 4

The vector pMON26106 has been introduced into canola and soybean callus via Agrobacterium transformation (Hinchee et al.). After selection of transformed cells using glyphosate and regeneration into whole plants, the seeds set by those plants will be analyzed.

Example 5

The vector pMON24502 has been introduced into wheat cells by microprojectile bombardment. Immature wheat embryos were isolated as described by Vasil et al. (1993). Embryogenic callus was obtained by culturing the immature embryos for 4 to 7 days, on a modified MS medium comprising about 40 g/l maltose and about 2 mg/l 2,4-D. The callus was subjected to bombardment with microprojectiles coated with pMON24502 and a plasmid containing a bialophos resistance gene. One day after bombardment the immature embryos were transferred to a growth medium containing the selective agent bialaphos. After seven days on the growth and selective medium the immature embryo-derived callus was removed to a shoot-producing medium (modified MS medium no 2,4-D) containing bialophos and grown for 28–40 days. A PCR assay will be done to confirm that the gtfA gene is present in the shoots. Shoots containing the gtfA gene will be rooted and taken to soil. When transformed plants are recovered and grown to maturity, their seeds will exhibit increased starch levels.

Example 6

The vector pMON24502 may be introduced into rice cells by microprojectile bombardment. Upon regeneration and selection, transformed plants will be assayed for expression of the gtfA gene and those plants demonstrating high expression will be grown to maturity. The seeds of the mature plants will exhibit increased starch levels.

Example 7

In order to evaluate the kinetic properties of two sucrose phosphorylase enzymes, the sucrose phosphorylase genes from Streptococcus mutans and Leuconostoc mesenteroides were separately cloned into pET15 expression vectors so that they could be overexpressed in E. coli.

The Leuconostoc mesenteroides gene sequence was obtained from Genbank (Accession Number D90314; Kitao et al., 1992) and nucleotide primers with homology to the 5' and 3' ends were designed for PCR amplification. Leuconostoc mesenteroides chromosomal DNA was extracted and the spl gene was amplified by PCR using the 5' oligonucleotide:

5' GGGGAGATCTAACCATGGAAATTCAAAA-CAAAGC 3' (SEQ ID NO:7)

and the 3' oligonucleotide:

5' GGGGGAGCTCATTAGTTCTGAGTCAAATTATC 3' (SEQ ID NO: 8).

The 1.5 kb PCR product was gel purified and digested with NcoI and SacI. The resulting restriction fragment was gel purified and ligated into the NcoI/SacI backbone of an E. coli expression vector, pMON5723, to form a vector construct which was used for transformation of component E. coli cells. The pMON5723 vector contains the E. coli recA promoter and the T7 gene 10 leader (G10L) sequences which enable high levels of expression in E. coli (Wong et al., 1988).

A 1491 bp NcoI/BamHI fragment containing the spl gene, encoding the Leuconostoc mesenteroides sucrose phosphorylase enzyme, was isolated from this vector construct using restriction digestion, gel purified, and cloned into the BamHI/NcoI backbone of the expression vector pET15b (obtained from Novagen), following manufacturer's instructions, resulting in the plasmid pMON21633. Similarly, a 1461bp NcoI/BamHI fragment containing the gtfA gene coding for the Streptococcus mutans sucrose phosphorylase, was cloned into the expression vector pET15b, resulting in the plasmid pMON21634. The resulting plasmids, pMON21633 and pMON21634, were transformed into 'subcloning efficiency'-DH5α competent cells (obtained from Gibco BRL), serving as a non-expression host to obtain establishment of the correct plasmids. Subsequently, these plasmid constructs were used for the transformation of competent BL21 (DE3) cells, a host strain provided with the pET system, to obtain high levels of expression. All DNA manipulations, cell transformation, selection etc. were performed according to the manufacturer's directions (Novagen).

For the purification of sucrose phosphorylase (Spl or GtfA), colonies of cells containing the correct plasmid construct were picked and used to grow liquid cultures (under Ampicillin selection), induced with IPTG (all purification steps were conducted at 4° C.). After growing an induced cell culture, the bacterial cell pellet was spun down and suspended in Buffer A (50 mM Tris-HCl, pH 7.5, 1 mM EDTA, 5% glycerol and 40 μl/ml protease inhibitor cocktail, purchased from Boehringer Mannheim Cat.#1-697-498)and cells were lysed using a French Press. The cell lysate was clarified by centrifugation at 15,000 rpm for 10 minutes.

Ammonium sulfate was added to the supernatant to reach 30% saturation, and the resultant mixture was then applied onto a phenyl-Sepharose 4B column which was pre-equilibrated with Buffer B (10 mM Tris-HCl, pH 8.0, 1 mM DTT and 1 mM EDTA) plus 20% (w/v) ammonium sulfate. The sucrose phosphorylase was eluted from the column with a linearly decreased ammonium sulfate gradient concentration from 20% to 0% in Buffer B. The fractions containing active sucrose phosphorylase were collected and pooled. Combined proteins were concentrated by precipitation with 70% saturation of ammonium sulfate followed by resuspension of the protein pellet in a small volume (2 or 4 ml) of Buffer C (10 mM Tris-HCl, 1 mM EDTA and 10% Glycerol). The sample was dialyzed in 2 liters of Buffer C two to three times (about 2 h for each) to completely remove ammonium sulfate prior to further purification. The dialyzed sample was injected into a Mono Q column which was pre-equilibrated with Buffer C. The sucrose phosphorylase was eluted from the column with a linear gradient of NaCl from 0 to 0.4 M in Buffer C. Sucrose phosphorylase active fractions were collected and analyzed by SDS-PAGE which indicated that the sucrose phosphorylase was at least 90% pure (at least 98% pure for Spl; at least 95% pure for GtfA), with molecular masses around 53 kDa.

Spl and GtfA activities were measured at 25° C. using a continuous spectrophotometric assay in which the production of glucose-1-phosphate from sucrose and inorganic phosphate is coupled to the production of NADP in the presence of phosphoglucomutase and glucose-6-phosphate dehydrogenase. The assay reaction mixture (1 ml final volume) contained 50 mM Hepes-NaOH pH 7.0, 50 mM sucrose, 5 mM MgCl2, 1 mM NADP, 20 mM Kpi monobasic pH 7.0 (50 mM for GtfA), 8 IU phosphoglucomutase, 2 IU glucose-6-phosphate dehydrogenase and appropriate amounts of Spl or GtfA. Production of NADPH was monitored spectrophotometrically at 340 nm. One unit of Spl or GtfA activity was defined as the amount of the enzyme which caused the reduction of 1 μmol of NADP per minute under the above conditions. A control reaction in which inorganic phosphate was omitted from the reaction mixture was always conducted for each Spl or GtfA assay.

Enzyme kinetic analysis yielded results shown in the following table. Unexpectedly, sucrose phosphorylase from S. mutans had a Vmax about 9 times lower than that of the enzyme from L. mesenteroides. In addition, the Km(sucrose) of the S. mutans enzyme was about 10 times lower than that of the L. mesenteroides enzyme.

| | $Km_{(sucrose)}$ (mM) | $Km_{(Pi)}$ (mM) | Vmax (U/mg) | $I_{0.5(Pi)}$ (mM) |
|---|---|---|---|---|
| *S. mutans* SP | 0.33 | 15.3 | 8.5 | ~70 |
| *L. mesenteroides* SP | 3.39 | 4.88 | 71.3 | ~55 |

Example 8

To further characterize the sucrose phosphorylases from S. mutans and L. mesenteroides, plasmid constructs containing the spl or the gtfA genes were made for protoplast transformation. A 1461 bp NcoI/BamHI fragment, containing the gtfA gene was isolated by restriction digestion, gel purified, and ligated to a 4646 bp BamHI/NcoI vector fragment containing the enhanced 35S promoter (e35S; Kay et al., 1987), the HSP70 intron (U.S. Pat. No. 5,593,874), the Nopaline synthase 3' region (Fraley et al., 1983), and a pUC vector derived backbone. A vector was thus created, containing the expression cassette [p-e35S/HSP70/gtfA/NOS3']. After ligation, the plasmid constructs were transformed into competent DH5α cells, and the transformed cells were plated out on Ampicillin-containing medium. From the colonies that were formed, positive clones were identified by restriction digest. In a similar experiment a 1491bp NcoI/BamHI fragment, containing the spl gene, was isolated by restriction digestion, gel purified, and ligated to the same 4646bp BamHI/NcoI vector fragment (described above). After ligation, transformation of competent cells, and identification of positive clones, the resulting plasmid constructs were used for corn leaf protoplast transformation. Corn leaf protoplast transformation was performed essentially as described by Sheen J., 1991, with some modifications to the protocol. The protoplast culture media was MS Fromm+0.6M mannitol (Fromm et al., 1987). Protoplast transformations were done in triplicate for both the gtfA and spl constructs.

Extraction buffer containing 100 mM Hepes pH 7.5, 1 mM EDTA, 5 mM DTT, 1 mM Benzamidine, 5% glycerol, and 40 μl/ml protease inhibitor cocktail solution at 1 tablet/2 ml (Boehringer Mannheim Cat.#1-697-498), was added to harvested protoplasts and the mixture was ground about 1–2 minutes. The protoplast homogenates were transferred into eppendorf tubes and spun at 14,000 rpm. To desalt the supernatant, spin columns (Boehringer Quick Spin Columns Cat. # 100973) were washed 3–5 times with double deionized $H_2O$, then once with 1 ml of extraction buffer. The buffer was removed from the spin column by centrifugation at 1400 rpm for 2 minutes. The protoplast extract was applied onto each column, spun at 1400 rpm for 2 minutes, and the passthrough was collected. 40 μl protease inhibitor cocktail stock solution (1 tablet/2 ml) was added into every ml of desalted extract. The desalted samples were used for enzyme assays.

Spl or GtfA activity was measured at 35° C. using a continuous spectrophotometric assay in which the production of glucose-1-phosphate from sucrose and inorganic phosphate is coupled to the production of NADP in the presence of phosphoglucomutase and glucose-6-phosphate dehydrogenase. The assay reaction mixture (1 ml final volume) contains 50 mM Hepes-NaOH pH 7.0, 100 mM sucrose, 5 mM MgCl2, 5 mM NaF, 1 mM NADP and 50 mM Kpi monobasic pH 7.0, 796 μl of reaction mix was mixed with a coupled enzyme mix (8 IU phosphoglucomutase, 2 IU glucose-6-phosphate dehydrogenase final concentrations) and 100 μl of the desalted protoplast extract. Sucrose (100 mM final concentration) was added to initiate the reaction. Production of NADPH was monitored spectrophotometrically at 340 nm. One unit of Spl or GtfA activity was defined as the amount of enzyme which caused the reduction of 1 μmol of NADP per minute under the above conditions. A control reaction in which inorganic phosphate was omitted from the reaction mixture was conducted for each assay. Under these reaction conditions (50 mM $P_i$) GtfA has optimal activity (100%), but Spl only reaches about 80% of its optimal activity.

The following results were obtained:

| Core Protoplasts | AU/min | Units/ml | Protein mg/ml | Units/mg protein | Average Units/mg protein |
|---|---|---|---|---|---|
| gtfA-1 | 0.0058 | 0.047 | 0.186 | 0.02526 | 0.03154 |
| gtfA-2 | 0.0062 | 0.0498 | 0.109 | 0.04567 | |

-continued

| Core Protoplasts | AU/min | Units/ml | Protein mg/ml | Units/mg protein | Average Units/mg protein |
|---|---|---|---|---|---|
| gtfA-3 | 0.0039 | 0.0039 | 0.313 | 0.0132 | |
| spl-1 | 0.0245 | 0.1967 | 0.082 | 0.23984 | 0.21753 |
| spl-2 | 0.0197 | 0.1582 | 0.082 | 0.19295 | |
| spl-3 | 0.0172 | 0.1385 | 0.063 | 0.21979 | |
| control | 0.0005 | 0.0038 | 0.228 | 0.00166 | |

As seen from the Table, Spl exhibits about a 7-fold increase in enzyme activity compared to GtfA in corn protoplasts.

Example 9

A vector was constructed for use in expressing spl and other sucrose phosphorylases in core, wheat or rice endosperm. For this, a 1588 bp BamHI/SmaI DNA fragment, containing the T7 gene 10 leader sequence (G10L) and the spl gene sequence, was isolated and ligated to an 8555 bp SmaI/BamHI vector fragment containing the HSP70 intron, the rice glutelin promoter Osgt-1 (Zheng et al., 1993), a pUC vector-derived backbone, and an expression cassette for the neomycin phosphotransferase type II gene (to confer Kanamycin resistance). From the resulting plasmid vector, a 10131 bp SstI/SmaI fragment was isolated and ligated to a 287 bp SmaI/SstI fragment, isolated from pMON999 (Rogers et al., 1987a), containing the NOS3' polyadenylation sequence. This created a plasmid vector, from which a 7831 bp NotI expression cassette [p-osgt-1/HSP70 intron/G10L/spl/NOS3'] was isolated and ligated into the NotI site of pMON30460, a monocot transformation vector, to form the plant transformation vector pMON17588. pMON30460 contains an expression cassette for the selectable marker neomycin phosphotransferase type II gene (KAN) [P-35S/NPTII/NOS3'] and a unique NotI site for cloning the gene of interest. The final vector (pMON17588) was constructed so that the gene of interest and the selectable marker gene could be easily cloned in the same orientation. A vector fragment containing the expression cassettes for these gene sequences can be excised from the bacterial selector (Kan) and ori, gel purified, and used for plant transformation.

Transgenic maize plants were produced using microprojectile bombardment, a procedure well-known in the art (Fromm et al., 1990; Gordon-Kamm et al., 1990; Walters et al., 1992). Embryogenic callus initiated from immature maize embryos was used as a target tissue. Plasmid DNA at 1 mg/ml in TE buffer was precipitated onto M10 tungsten particles using a calcium chloride/spermidine procedure, essentially as described by Klein et al. (1988). In addition to the gene of interest, the plasmids also contained the neomycin phosphotransferase II gene (nptII) driven by the 35S promoter from Cauliflower Mosaic Virus. The embryogenic callus target tissue was pre-treated on culture medium osmotically buffered with 0.2M mannitol plus 0.2M sorbitol for approximately four hours prior to bombardment (Vain et al., 1993). Tissue was bombarded two times with the DNA-coated tungsten particles using the gunpowder version of the BioRad Particle Delivery System (PDS) 1000 device. Approximately 16 hours following bombardment, the tissue was subcultured onto a medium of the same composition except that it contained no mannitol or sorbitol, and it contained an appropriate aminoglycoside antibiotic, such as G418" to select for those cells which contained and expressed the 35S/nptII gene. Actively growing tissue sectors were transferred to fresh selective medium approximately every 3 weeks. About 3 months after bombardment, plants were regenerated from surviving embryogenic callus essentially as described by Duncan and Widholm (1988).

Kernels (R1 seed) were harvested from R0 maize plants, transformed with the construct pMON17588, which contains the spl gene linked to the endosperm-specific rice glutelin promoter and the HSP70 intron. The kernels were screened by both sucrose phosphorylase activity assays and Western blot analysis. For this, kernels were harvested at 20 DAP (days after pollination) from one plant per line and approximately 8 kernels per plant. Each sample was initially screened for Spl activity. Samples with no activity were indentified as non-expressors and those showing Spl enzyme activity were further screened by Spl western blot analysis. A significant correlation was observed between Spl enzyme activity and Spl protein levels, i.e., all the samples with high Spl enzyme activity also showed high Spl protein levels by Western blot analysis. Out of 64 plants that were screened, 31 showed both Spl enzyme activity and Spl protein by these analyses.

Example 10

Maize lines expressing the gtfA transgene [Osgt1/HSP70/gtfA/NOS3'] described in Example 1 (derived from pMON24502) up to approximately 0.5% of the total protein levels have been identified and one homozygous R2 line "Majorie" was evaluated by an in vitro culture system as described by Cheikh and Jones, 1995 and Jones et al., 1981.

Analysis of the developmental profile of maize kernels expressing the gtfA transgene, line "Majorie", compared to that of the negative (non-transgenic) controls, demonstrated higher dry weight (−15%) at physiological maturity (45 DAP, days after pollination) in the gtfA expressors.

| | Dry Weight (mg/kernel) |
|---|---|
| Negative control | 105.8 ± 310 |
| gtfA expressors | 120.3 ± 2.55 |

As shown in FIG. 1, Western analysis of kernels sampled at 12, 25, 35 and 45 DAP revealed that elevated GtfA levels were detectable between 12 and 45 DAP.

Analysis of kernel developmental variation in nonstructural carbohydrate levels showed significantly higher levels of fructose and starch and lower levels of sucrose during the period of gtfA expression, but no significant pattern of variation in glucose content (see Tables below). These patterns of variations reflect the activity and the effect of the gtfA transgene in the maize endosperm.

Changes in starch levels of maize kernels expressing gtfA as compared to those of negative controls are shown in the following Table:

| | Kernel Starch (mg/g dry weight) | | | |
|---|---|---|---|---|
| | Negative | | Kernel Starch (mg/grain) | |
| DAP | Control | gtfA positive | Negative Control | gtfA positive |
| 20 | 416.9 ± 11.9 | 424.5 ± 12.7 | 16.42 ± 0.91 | 17.53 ± 0.87 |
| 24 | 524.5 ± 2.6 | 558.4 ± 12.4 | 34.10 ± 1.17 | 32.94 ± 0.46 |
| 28 | 523.4 ± 9.3 | 553.0 ± 8.7 | 41.38 ± 2.96 | 40.55 ± 0.92 |

-continued

| | Kernel Starch (mg/g dry weight) | | | |
|---|---|---|---|---|
| | Negative | | Kernel Starch (mg/grain) | |
| DAP | Control | gtfA positive | Negative Control | gtfA positive |
| 35 | 533.6 ± 9.3 | 576.0 ± 3.9 | 45.57 ± 2.56 | 55.20 ± 0.84 |
| 40 | 540.5 ± 9.7 | 592.5 ± 9.1 | 57.11 ± 1.37 | 69.68 ± 2.16 |

Changes in soluble carbohydrate levels of maize kernels expressing gtfA as compared to those of negative controls were also evaluated and the results are shown in the following Table:

| DAP | | Glucose (mg/kernel) | Fructose (mg/kernel) | Sucrose (mg/kernel) |
|---|---|---|---|---|
| 12 | Negative | 2.53 ± 0.15 | 1.87 ± 0.10 | 1.36 ± 0.12 |
| | Positive | 2.15 ± 0.06 | 1.60 ± 0.03 | 1.25 ± 0.15 |
| 20 | Negative | 1.68 ± 0.14 | 0.93 ± 0.09 | 1.49 ± 0.20 |
| | Positive | 1.76 ± 0.09 | 1.17 ± 0.05 | 0.89 ± 0.06 |
| 24 | Negative | 2.11 ± 0.09 | 0.98 ± 0.32 | 1.58 ± 0.12 |
| | Positive | 1.68 ± 0.05 | 1.08 ± 0.04 | 0.53 ± 0.05 |
| 28 | Negative | 1.80 ± 0.12 | 0.68 ± 0.04 | 1.31 ± 0.10 |
| | Positive | 1.93 ± 0.06 | 1.20 ± 0.37 | 0.58 ± 0.07 |
| 35 | Negative | 1.40 ± 0.08 | 0.49 ± 0.33 | 1.47 ± 0.10 |
| | Positive | 2.03 ± 0.09 | 1.09 ± 0.03 | 0.70 ± 0.09 |
| 40 | Negative | 0.69 ± 0.12 | 0.30 ± 0.03 | 1.41 ± 0.07 |
| | Positive | 0.63 ± 0.05 | 0.30 ± 0.03 | 1.45 ± 0.06 |

All publications and patents mentioned in this specification are herein incorporated by reference as if each individual publication or patent was specifically and individually stated to be incorporated by reference.

From the foregoing, it will be seen that this invention is one well adapted to attain all the ends and objects hereinabove set forth together with advantages which are obvious and which are inherent to the invention.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

BIBLIOGRAPHY

Ammirato, P. V., et al. Handbook of Plant Cell Culture—Crop Species, Macmillan Publ. Co. (1984).
Benfey, P., Ren, L., and Chua, N. H. (1989) EMBO J, 5: 2195–2202.
Bevan, M. (1984) Nucleic Acids Res.12 (22): 8711–8721, 12(22): 8711–8721.
Bevan, et al. (1986) Nucleic Acids Res., 14 (11):4625–4638.
Blennow, A. and Johansson, G. (1991) Phytochemistry 30:437–444.
Cheikh N and Jones R J 1995. Heat stress effects on sink activity of developing maize kernels grown in vitro. Physiologia Plantarum 95:59–66.
Datta, et al. (1990) Biotechnology 8:736–740.
Deikman, J. and R. L. Fischer. (1988) EMBO J 7: 3315–3320.
Denneby et al. (1994) Plant Cell Tiss. & Organ Cult. 36:1–7.
Duncan et al. (1985) Planta 165:322–332.
Duncan and Widholm (1988) Plant Cell Reports 7: 452–455.
Ebbelaar, et al. (1993) Int. Symp. on Gen. Manip. of Plant Metabolism and Growth, 29–31 March, Norwich UK, Abstract #9.
Felker, F. C., Liu, K. C., and Shannon, J. C. (1990) Plant Physiology 94, 996–1001.
Ferretti, et al. (1988) Infection and Immun. 56:1585–1588.
Fournier, et al. (1994) Mol. Plant-Microbe Inter. 7:164–172.
Fraley, et al. (1983). PNAS USA 80: 4803–4807.
Fraley, et al. (1985). Bio/Technology 3:629–635.
Fraley, et al. (1986). Critical Reviews in Plant Sciences 4: 1–46.
Fromm, et al. (1987). Methods in Enzymology Vol.153: 351–356.
Fromm et al. (1990) Bio/Technology 8: 833–839.
Fromm, M., (1990) UCLA Symposium on Molecular Strategies for Crop Improvement, Apr. 16–22, 1990. Keystone, Colo. 1990. Keystone, Colo.
Gordon-Kamm et al. (1990) Plant Cell 2: 603–618.
Hannapel, D. J. (1990) Plant Phys. 94: 919–925.
Hayashimoto, A., Z. Li, Murai, N. (1990) Plant Physiol. 93:857–863.
Herrera-Estrella, L., et al. (1983) Nature 303:209.
Hinchee et al. (1988) Biotechnology 6:915–922.
Horsch, R. B. and H. M. Klee. (1986) PNAS U.S.A. 83:4428–32.
Iglesias, et al., (1993) J. Biol Chem. 268:1081–1086.
Jefferson, et al. (1990) Plant Mol. Biol. 14: 995–1006.
Jones R J, Gengenbach B G and Cardwell V B 1981. Temperature effects on in vitro kernel developemtn of maize. Crop Science 21:761–766.
Kay, R., A. Chan, M. Daly and J. McPherson. (1987) Science 236:1299–1302.
Kitao, S. and E. Nakano (1992) J. Ferment. Bioeng. 73:179–84.
Klee, H. J., et al. (1985) Bio/Technology 3:637–42.
Klee, H. J., and Rogers, S. G. (1989). Plant gene vectors and genetic transformation: Plant transformation systems based on the use of Agrobacterium tumefaciens. Cell Culture and Somatic Cell, Genetics of Plants 6, 1–23.
Klein et al. (19898) Bio/Technology 6: 559–563.
Maniatis et al. Molecular Cloning: A Laboratory Manual. Cold Spring Harbor Laboratory Press, Cold Spring Harbor, N.Y., 1982.
Mein et al. (1989) Bio/Technology 6: 559–563.
Kossmann et al. (1991) Mol. Gen. Genet. 230:39–44.
Mignery, et al (1988) Gene 62:27–44.
Mori et al. (1991) J. Biol. Chem., 266: 18446–18453.
Muller, et al (1990) Mol. Gen Genet. 224:136–146.
Nakamura, K., and Matsuoka, K. (1993) Plant Physiol., 101:1–5.
Nakano et al. (1989) J. Biochem. 106: 691–695.
Ohta et al. (1991) Mol. Gen. 225: 369–378.
Ohshima et al. (1990) Nucleic Acid Research 18: 181.
Pear, et al. (1989) Plant Mol. Biol. 13:639–651.
Pedersen, et al. (1982) Cell 29: 1015–1026.
Perry, D. and H. K. Kuramitsu (1990) Infect. Immun. 58(10) :3462–4.
Pimentel, et al. (1992) Revista de Microbiologia 23:199–205.
Robeson, et al. (1983) J. Bacteriol. 153:211–221.
Rocha-Sosa, et al. (1989) EMBO J. 8 (1):23–29.

Rogers, S. G., H. J. Klee, R. B. Horsch, and R. T. Fraley. (1987a) Improved Vectors for Plant Transformation: Expression Cassette Vectors and new Selectable Markers. In Methods in Enzymology. Edited by R. Wu and L. Grossman. 253–277, San Diego: Academic Press, Rogers, S., et al. (1987) In 153 Methods in Enzymology: Edited by H. Weissbach and A. Weissbach. 253: Academic Press.
Rogers, S., and Klee, H. (1987). Pathways to genetic manipulation employing Agrobacterium. Plant Gene Research, Plant DNA Infectious Agents, Vol IV. Hohn, T. and J. Schell, eds. Springer-Verlag, Vienna, 179–203.
Rohde et al. (1990) J. Genet. & Breed. 44:311–315.
Russell, et al. (1988) Infect. Immun. 56(10):2763–5.
Samac, et al. (1990) Plant Physiol. 93:907–914.
Sambrook et al., Molecular cloning: A laboratory manual, 2nd ed., Cold Spring Harbor Laboratory Press, Cold Spring Harbor, N.Y., 1989.
Schmidhauser, T. J. and D. R. Helinski. (1985) J. Bacteriol. 164–155.
Shahar et al. (1992) Plant Cell 4:135–147.
Sheen, J. (1991). The Plant Cell Vol.3: 225–245.
Shimamoto, K., et al. (1989) Nature 338:274–276.
Silverstein, R., et al. (1967) J. Biol. Chem. 242:1338–1346.
Solanoubat, M. and G. Belliard (1987) Gene 60:47–56.
Solanoubat, M. and G. Belliard (1989) Gene 84:181–185.
Sonnewald et al. (1991) Plant J. 1:95–106.
Stiekema et al. (1988) Plant Mol. Biol. 11: 255–269.
Stukerlj et al. (1990) Nucl. Acids Res. 18:46050.
Takaha et al., (1993) J. Biol. Chem. 26 8:1391–1396.
Tierney, et al. (1987) Planta 172:356–363.
Vain et al. (1993) Plant Cell Reports 12: 84–88.
Vandamme, et al. (1987) Adv. Appl. Microbiol. 32:163–201.
Vasil, V., F. Redway and I. Vasil. (1990) Bio/Technology 8:429–434.
Vasil et al. (1992) Bio/Technology 10:667–674.
Vasil, et al. (1993) Bio/Technology 11: 1153–1158.
Walters et al. (1992) Plant Molecular Biology 18: 189–200.
Yoshida et al. (1992) Gene 10: 255–259.
Zheng et al. (1993) Plant J. 4: 3357–366.

SEQUENCE LISTING

```
<160> NUMBER OF SEQ ID NOS: 8

<210> SEQ ID NO 1
<211> LENGTH: 29
<212> TYPE: DNA
<213> ORGANISM: Artificial Sequence
<220> FEATURE:
<223> OTHER INFORMATION: Synthetic

<400> SEQUENCE: 1

cccggatcca tggcaattac aaataaaac                                        29


<210> SEQ ID NO 2
<211> LENGTH: 39
<212> TYPE: DNA
<213> ORGANISM: Artificial Sequence
<220> FEATURE:
<223> OTHER INFORMATION: Synthetic

<400> SEQUENCE: 2

ggggagctca ctcgaagctt attgtttgat cattttctg                             39


<210> SEQ ID NO 3
<211> LENGTH: 1478
<212> TYPE: DNA
<213> ORGANISM: Lycopersicon esculentum

<400> SEQUENCE: 3

agccttgtgt taggggtat tcaaaccttc tttgactgaa aattttatta tttatacatg      60

tttaaaatta ctttttaatc tatatataat agatatcaat ccttcattta attgtatttt     120

tgtattaatt ctataaatat taaattactt tattaaaaat tctaattctg tcactcgtca     180

tttcataata ttcttgacgg tgatggtagt gataattacg ttgattggag ccacatgggc     240

cgctactttt taaaaggatg aaccttggaa tgtagtgaat gttgagtctc atagctcact     300

cacggactca acagcaaaat ctgtcctctt tttcccttct ccaattcaca tactgtcact     360

tggacaaata atatttgaaa attttggcct aaagttaggt ttggagccgt atggtaattt     420

gatacacaaa ttattatata attgatatat caggtatata tatcaagttg tcgcttcttc     480

gttcattgtt tctctcacta aaattttcaa ttcacttttt aaaaaatcga taaattttta     540
```

-continued

```
atataacttt acataacata ttcaaaatta caaaaataaa ggatattttt atatgtttat    600

ttttaatgta agattaaata tttagaattc tttttaagaa cggtacaagc aaattaaaag    660

agagaaggta tattagtggg cctatgtatc tttgatatca tatgcctctc aaagagcatc    720

ctgatgagtc tatatatctt tgttgatagt gatttaacca tttatgtatg tacgtagtac    780

taagacatgt taaataagat cctagagaaa gatttttgga aaagtgaaaa cagcaataaa    840

gaaaagtcat ttaaacactt tccaacaaac atttggtaat cgattttaat tacccactta    900

aacaaaacta tttgtacgta aaatgtttaa gtagaaaaga gatttttta aaaaaaaaaa    960

gaaggcaaga ggtcatatat ctgacccttc cttaaatccc cgcgtataac actttctttt   1020

ttttgtgtgt gtatgttcag gaacatttgt attttctatt tgaaatttct cattaagtca   1080

aattcgaaat cttttaaata atgtagagaa atctcattat atttaacaat cccacttgat   1140

gaattcctaa acattttcta taaaataaca ctaaatcttt aattatacat attacatacc   1200

taactcaagc aatcttgtcg gaaaaatcat tagaaaagaa ttggaaatag ggaaataaat   1260

agacatattt tggttagtat ctttgtctat aagaatgggt gtgttaaaga gctagtgcca   1320

tagtgtacca ttctattggt agcatttggc aagagttatt ccctctctcc ataccaatgg   1380

agaagtttaa tcttgctaga gtcttattgt tgcttcttca acttggaact ttgttcattg   1440

cccatgcatg tccttattgt ccatatcctc cttccacc                           1478
```

<210> SEQ ID NO 4
<211> LENGTH: 450
<212> TYPE: DNA
<213> ORGANISM: Lycopersicon esculentum

<400> SEQUENCE: 4

```
aaataaatat ttcaaagtaa attgttactc cctctatccc atactctttt ctttttttaa     60

tcgatttctt actctaattg aactattgga gacaacttaa atgtaaattt tttttttctt    120

tatcaaaatg attggctgct atataaatat ctaatggtta ttatacataa attttaatat    180

tttttataaa aaaatatcga gctaaatcat atcgtttaaa tatagagatg tgttatttat    240

ttaaaaatta attttaaaaa agtgaatatt gtaaattagg atgaaagagt attatattgg    300

ttgtcgcagt ataaataccc tgcatgccat tacatttgtt caatcatctt tgcaacgatt    360

tgtgtgcttt agcttcctta cataacatgg cttctataac taaagcctca ttacttatcc    420

ttttcctctc cttgaatctc cttttcttcg                                     450
```

<210> SEQ ID NO 5
<211> LENGTH: 1446
<212> TYPE: DNA
<213> ORGANISM: Streptococcus mutans

<400> SEQUENCE: 5

```
atggcaatta caaataaaac aatgttgatt acttacgcag acagtttggg taaaaatttg     60

aaagaattga atgaaaatat tgagaattat tttgcagatg ctgttggcgg tgtccatttg    120

ctgccattct ttccttccac aggtgatcgt ggctttgcac cgattgatta ccatgaagtt    180

gactctgctt ttggcgattg ggatgatgtc aaacgtttgg gtgaaaaata ttacctcatg    240

tttgatttca tgattaatca tatttcgcgt cagtctaaat attataaaga ttaccaagaa    300

aagcatgaag caagtgctta taaagatcta tttttaaatt gggataaatt ttggcctaaa    360

aatcgcccga cacaagaaga tgtggacctg atttataagc gtaaggatcg agcacctaag    420
```

-continued

```
caggaaatcc aatttgcaga tggcagtgtt gaacatctct ggaacacttt tggggaggaa    480
cagattgatc ttgacgtgac taaagaagtg actatggatt ttattcgctc taccattgaa    540
aatttagcag ccaacggctg tgatctcatt cgtttggatg ccttgcttta tgctgttaaa    600
aagctagata cgaatgattt ctttgttgaa cctgaaatct ggactctgct agataaagtt    660
cgtgatatag ctgctgtatc gggtgcggaa atcttgccgg aaattcatga acactatact    720
attcaattta aaattgcaga ccatgattac tatgtttatg attttgccct gcctatggtg    780
acgctctaca gcctatattc gggcaaggtt gaccgtcttg ccaaatgggt gaaaatgagt    840
ccgatgaaac agttcaccac ccttgataca catgacggta ttggtgtggt tgatgttaag    900
gatatcctga ctgacgaaga aattacctat acttctaatg agctttataa ggtcggtgcc    960
aatgtcaatc gtaagtattc aactgccgaa tataataact tggatatcta tcaaattaat   1020
tcaacttact attcagcact tggtgatgat gatcaaaaat actttttggc ccggttgata   1080
caagcttttg ctccaggtat tccacaggtt tattacgttg gctttttagc tggcaagaat   1140
gatcttgaat tactggaaag cactaaagaa ggccgcatta tcaaccgtca ttattatagt   1200
agtgaagaaa ttgctaagga agtgaagcgg ccagttgtca aggcactttt aaatctcttt   1260
acttaccgca ttcagtcagc agcttttgat ttggatggcc gtattgaagt ggaaacgcca   1320
aatgaagaga acattgtcat agaacgtcaa aataaagatg gcagtcatat cgcaacagca   1380
gagattaatc tccaagatat gacatacaga gtaacagaaa atgatcaaac aataagcttc   1440
gagtga                                                              1446
```

<210> SEQ ID NO 6
<211> LENGTH: 1473
<212> TYPE: DNA
<213> ORGANISM: Leuconostoc mesenteroides

<400> SEQUENCE: 6

```
atggaaattc aaaacaaagc aatgttgatc acttatgctg attcgttggg caaaaactta     60
aaagatgttc atcaagtctt gaaagaagat attggagatg cgattggtgg ggttcatttg    120
ttgcctttct tcccttcaac aggtgatcgc ggttttgcgc cagccgatta tactcgtgtt    180
gatgccgcat ttggtgattg ggcagatgtc gaagcattgg gtgaagaata ctatttgatg    240
tttgacttca tgattaacca tatttctcgt gaatcagtga tgtatcaaga ttttaagaag    300
aatcatgacg attcaaagta taaagatttc tttattcgtt gggaaaagtt ctgggcaaag    360
gccggcgaaa accgtccaac acaagccgat gttgacttaa tttacaagcg taaagataag    420
gcaccaacgc aagaaatcac ttttgatgat ggcacaacag aaaacttgtg gaatactttt    480
ggtgaagaac aaattgacat tgatgttaat tcagccattg ccaaggaatt tattaagaca    540
acccttgaag acatggtaaa acatggtgct aacttgattc gtttggatgc ctttgcgtat    600
gcagttaaaa aagttgacac aaatgacttc ttcgttgagc cagaaatctg ggacactttg    660
aatgaagtac gtgaaatttt gacaccatta aaggctgaaa ttttaccaga aattcatgaa    720
cattactcaa tccctaaaaa gatcaatgat catggttact tcacctatga ctttgcatta    780
ccaatgacaa cgctttacac attgtattca ggtaagacaa atcaattggc aaagtggttg    840
aagatgtcac caatgaagca attcacaaca ttggacacgc atgatggtat tggtgtcgtt    900
gatgcccgtg atattctaac tgatgatgaa attgactacg cttctgaaca actttacaag    960
gttggcgcga atgtcaaaaa gacatattca tctgcttcat acaacaacct tgatatttac   1020
caaattaact caacttatta ttcagcattg ggaaatgatg atgcagcata cttgttgagt   1080
```

-continued

```
cgtgtcttcc aagtctttgc gcctggaatt ccacaaattt attacgttgg tttgttggca   1140

ggtgaaaacg atatcgcgct tttggagtca actaaagaag gtcgtaatat taaccgtcat   1200

tactatacgc gtgaagaagt taagtcagaa gttaagcgac cagttgttgc taacttattg   1260

aagctattgt catggcgtaa tgaaagccct gcatttgatt tggctggctc aatcacagtt   1320

gacacgccaa ctgatacaac aattgtggtg acacgtcaag atgaaaatgg tcaaaacaaa   1380

gctgtattaa cagccgatgc ggccaacaaa acttttgaaa tcgttgagaa tggtcaaact   1440

gttatgagca gtgataattt gactcagaac taa                                1473


<210> SEQ ID NO 7
<211> LENGTH: 34
<212> TYPE: DNA
<213> ORGANISM: Artificial Sequence
<220> FEATURE:
<223> OTHER INFORMATION: Synthetic

<400> SEQUENCE: 7

ggggagatct aaccatggaa attcaaaaca aagc                                 34


<210> SEQ ID NO 8
<211> LENGTH: 32
<212> TYPE: DNA
<213> ORGANISM: Artificial Sequence
<220> FEATURE:
<223> OTHER INFORMATION: Synthetic

<400> SEQUENCE: 8

gggggagctc attagttctg agtcaaatta tc                                   32
```

What is claimed is:

1. A method of producing a transgenic plant, comprising the steps of:

(a) stably transforming into the genome of a plant cell a recombinant, double-stranded DNA molecule comprising:

(i) a promoter which functions in cells of target plant tissue, (ii) a structural DNA sequence obtained from a bacterium of the genus Leuconostoc that causes the production of an RNA sequence which encodes a sucrose phosphorylase enzyme, (iii) a 3' non-translated DNA sequence which functions in plant cells to cause transcriptional termination and the addition of polyadenylated nucleotides to the 3' end of the RNA sequence;

(b) selecting for transformed plant cells; and (c) regenerating from said transformed plant cells a genetically transformed plant, the genome of which contains said recombinant, double-stranded DNA molecule of step (a), wherein said genetically transformed plant exhibits [a property] *one or more properties* selected from the group consisting of containing a modified carbohydrate content; increased polysaccharide content; enhanced yield of harvested material; improved uniformity of the distribution of solids; *increased oil content; increased protein content;* and reduced susceptibility to bruising discoloration.

2. The method of claim 1, wherein said DNA sequence is obtained from Leuconostoc mesenteroides.

3. The method of claim 2, wherein said DNA sequence comprises the sequence shown in SEQ ID NO:6.

4. The method of claim 1, wherein said property is containing a modified carbohydrate content.

5. The method of claim 4, wherein said modified carbohydrate content is an increase in solids content.

6. The method of claim 5, wherein said genetically transformed plant is selected from the group consisting of potato and tomato.

7. The method of claim 1, wherein said property is improved uniformity of the distribution of solids.

8. The method of claim 7, wherein said genetically transformed plant is selected from the group consisting of potato and sweet potato.

9. The method of claim 1, wherein said property is reduced susceptibility to bruising discoloration.

10. The method of claim 9, wherein said genetically transformed plant is selected from the group consisting of potato, banana, apple, wheat, grape, and peach.

11. The method of claim 1, wherein said property is increased polysaccharide content.

12. The method of claim 11, wherein said genetically transformed plant is selected from the group consisting of maize, wheat, rice, tomato, potato, sweet potato, peanut, barley, cotton, strawberry, raspberry, and cassava.

13. The method of claim 1, wherein said property is enhanced yield of harvested material.

14. The method of claim 13, wherein said genetically transformed plant is selected from the group consisting of maize, wheat, rice, tomato, potato, sweet potato, peanut, barley, sugarbeet, sugarcane, apple, pear, orange, peach, grape, cotton, strawberry, raspberry, and cassava.

15. The method of claim 1, wherein said plant cell is selected from the group consisting of a potato plant cell, a maize plant cell, a rice plant cell, a wheat plant cell, a tomato plant cell, a barley plant cell, a sugarbeet plant cell, a sweetpotato plant cell, a peanut plant cell, a sugarcane plant cell, a grape plant cell, a pear plant cell, an apple plant cell, an orange plant cell, a cassava plant cell, a banana plant cell, a plantain plant cell, a cotton plant cell, a strawberry plant cell, a raspberry plant cell, and a peach plant cell.

16. The method of claim 15, wherein said plant cell is a potato plant cell.

17. The method of claim 15, wherein said plant cell is a maize plant cell.

18. The method of claim 15, wherein said plant cell is selected from the group consisting of a wheat plant cell, a barley plant cell, a rice plant cell, and a tomato plant cell.

19. A recombinant, double-stranded DNA molecule comprising in sequence:

(a) a promoter which functions in cells of target plant tissue;

(b) a structural DNA sequence obtained from a bacterium of the genus Leuconostoc that causes the production of an RNA sequence which encodes a sucrose phosphorylase enzyme; and (c) a 3' non-translated region which functions in plant cells to cause transcriptional termination and the addition of polyadenylated nucleotides to the 3' end of the RNA sequence.

20. The DNA molecule of claim 19, wherein said DNA sequence is obtained from Leuconostoc mesenteroides.

21. The DNA molecule of claim 20, wherein said DNA sequence comprises the sequence shown in SEQ ID NO:6.

22. The DNA molecule of claim 19, wherein said promoter is selected from the group consisting of a zein promoter, a patatin promoter, a rice glutelin promoter, the soybean 7s promoter, a promoter of a subunit of ADPglucose pyrophosphorylase, the TFM7 promoter, and the TFM9 promoter.

23. A transformed plant cell comprising a recombinant, doublestranded DNA molecule comprising in sequence:

(a) a promoter which functions in said plant cell;

(b) a structural DNA sequence obtained from a bacterium of the genus Leuconostoc that causes the production of an RNA sequence which encodes a sucrose phosphorylase enzyme; and (c) a 3' non-translated region which functions in plant cells to cause transcriptional termination and the addition of polyadenylated nucleotides to the 3' end of the RNA sequence.

24. The plant cell of claim 23, wherein said DNA sequence is obtained from Leuconostoc mesenteroides.

25. The plant cell of claim 24, wherein said DNA sequence comprises the sequence shown in SEQ ID NO:6.

26. The plant cell of claim 23, wherein said promoter is selected from the group consisting of a zein promoter, a patatin promoter, a rice glutelin promoter, the soybean 7s promoter, a promoter of a subunit of ADPglucose pyrophosphorylase, the TFM7 promoter, and the TFM9 promoter.

27. The plant cell of claim 23, wherein said plant cell is selected from the group consisting of a potato plant cell, a maize plant cell, a rice plant cell, a wheat plant cell, a tomato plant cell, a barley plant cell, a sugarbeet plant cell, a sweetpotato plant cell, a peanut plant cell, a sugarcane plant cell, a grape plant cell, a pear plant cell, an apple plant cell, an orange plant cell, a cassava plant cell, a banana plant cell, a plantain plant cell, and a peach plant cell.

28. A transformed plant comprising a recombinant, doublestranded DNA molecule comprising in sequence:

(a) a promoter which functions in said plant cell;

(b) a structural DNA sequence obtained from a bacterium of the genus Leuconostoc that causes the production of an RNA sequence which encodes a sucrose phosphorylase enzyme; and (c) a 3' non-translated region which functions in plant cells to cause transcriptional termination and the addition of polyadenylated nucleotides to the 3' end of the RNA sequence.

29. The plant of claim 28, wherein said DNA sequence is obtained from Leuconostoc mesenteroides.

30. The plant cell of [claims] *claim* 29, wherein said DNA sequence comprises the sequence shown in SEQ ID NO:6.

31. The plant of claim 28, wherein said promoter is selected from the group consisting of a zein promoter, a patatin promoter, a rice glutelin promoter, the soybean 7s promoter, a promoter of a subunit of ADPglucose pyrophosphorylase, the TFM7 promoter, and the TFM9 promoter.

32. The plant of claim 28, wherein said plant is selected from the group consisting of a potato plant, a maize plant, a rice plant, a wheat plant, a tomato plant, a barley plant, a sugarbeet plant, a sweetpotato plant, a peanut plant, a sugarcane plant, a grape plant, a pear plant, an apple plant, an orange plant, a cassava plant, a banana plant, a plantain plant, and a peach plant.

33. The method of claim 1, wherein the polysaccharide is starch.

34. The method of claim 11, wherein the polysaccharide is starch.

*35. The method of claim 1, wherein the property is increased oil content.*

*36. The method of claim 1, wherein the property is increased protein content.*

*37. The method of claim 1, wherein said plant cell is a canola plant cell.*

*38. The method of claim 1, wherein said plant cell is a soybean plant cell.*

*39. The plant cell of claim 23, wherein said plant cell is a canola plant cell.*

*40. The plant cell of claim 23, wherein said plant cell is a soybean plant cell.*

*41. The plant of claim 28, wherein said plant is a canola plant.*

*42. The plant of claim 28, wherein said plant is a soybean plant.*

*43. The method of claim 1, wherein the one or more properties are modified carbohydrate content and increased oil content.*

*44. The method of claim 1, wherein the one or more properties are modified carbohydrate content and increased protein content.*

* * * * *